(12) United States Patent
Feiring et al.

(10) Patent No.: US 6,875,555 B1
(45) Date of Patent: Apr. 5, 2005

(54) PREPARATION AND USE OF EXO-2-FLUOROALKYL(BICYCLO[2.2.1]HEPT-5-ENES)

(75) Inventors: Andrew Edward Feiring, Wilmington, DE (US); Viacheslav Alexandrovich Petrov, Hockessin, DE (US); Frank Leonard Schadt, III, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 14 days.

(21) Appl. No.: 10/664,303

(22) Filed: Sep. 16, 2003

(51) Int. Cl.$^7$ .................. G03F 7/004; C08F 214/18

(52) U.S. Cl. .................. 430/270.1; 430/325; 430/326; 430/320; 526/242; 526/281

(58) Field of Search ............................. 430/270.1, 325, 430/326, 907; 526/281, 242

(56) References Cited

U.S. PATENT DOCUMENTS

| | | |
|---|---|---|
| 5,726,344 A | 3/1998 | West et al. |
| 2002/0102490 A1 | 8/2002 | Ito et al. |

OTHER PUBLICATIONS

"Synthesis and Evaluation of Alicyclic Backbone Polymers for 193 nm Lithography" Hiroshi Ito, Norbert Seehof, Rikiya Sato, Tomonari Nakayama and Mitsuru Ueda American Chemical Society (1998) Chapter 16, pp208–223.

Journal Article (Abstract) "Vinyl Polymerization. LXXX-VIII. Polymerization and Copolymerization of Endo– and Exo–5–Cyanobicyclo[2.2.1]hept–2–ene" Imoto, Minoru; Otsu, Takayuki; Ito, Toshio, Kogyo Kagaku Zasshi (1964), 67(6), 961–5.

Journal Article (Abstract) "Vinyl Polymerization. LXXII. Preparation and Polymerization of Vinyl Bicyclo[2.2.1] Heptane–2–Carboxylate", Imoto, Minoru; Otsu, Takayuki; Fukuda, Wakichi, Kogyo Kagaku Zasshi (1963), 66(6), 832–6.

Neal Brace, J. Org. Chem. 27, (1962), 3027–3032, "Free Radical Addition of Iodoperfluoroalkanes to Bicyclic Olefins".

S. Breunig et al. Makromol. Chem. 193, 2915–2927 (1992) "Transition–metal–catalyzed vinyl addition polymerizations of norbornene derivatives with ester groups".

American Chemical Society (1985) 3269–3274, Andrew E. Feiring, "Reaction of Perfluoroalkyl Iodides with Electron Donor Nucleophiles. Addition of Perfluoroalkyl Iodides to Olegins Initiated by Electron Transfer".

Journal of Photopolymer Science and Technology, vol. 13, No. 4 (2000) 657–664, Takashi Chiba et al. 157 nm Resist Materials: A Progress Report.

Robert L. Augustine, "Catalytic Hydrogenation", Marcel Dekker, Inc. New York (1965), 125–146.

Louis Schmerling, J.P. Luviri and Robert W. Welch, "Some Reactions of 2,5–Norbornadiene (Bicyclo[2.2.1]–2,5–heptadiene)" (1956) Contribution from the Research and Development Laboratories, Universal Oil Products Co.

Viacheslav A. Petrov, Synthesis 2002, No. 15, 2225–2231, ISSN0039–7881 "Synthesis of Polyfluorinated Tertiary Alcohols Using Ring Opening Reactions of 2,2–Bis(trifluoromethyl)Oxirane".

Richard A. Bartsch and John Gun Lee, J. Org. Chem (1991) 212–217 "Stereochemistry of Base–Promoted 1,2–Elimination from exo–2–Bicyclo[2.2.1]heptyl Tosylate and Choride".

Neal O. Brace, Journal of Fluorine Chemistry, 20 (1982) 313–327 "Some Approaches to the Synthesis of Fluorinated Alcohols and Esters. II. Use of F–Alkyl Iodines for the Synthesis of F–Alkyl Alkanols".

Raymond J. Hung et al., "Resist Materials for 157 nm Microlithography: An Update" Proceedings of SPIE vol. 4345 (2001) 385–395.

John D. Roberts, E.R. Trumbull, Jr., Winnifred Bennett and Rose Armstrong, "The Reaction of Norbornylane with N–Bromosuccinimide. Nortricyclene and Its Derivatives" (1950) vol. 72, 3116–3124 Contribution from the Department of Chemistry and Laboratory of Nuclear Science and Engineering, Massachusetts Institute of Technology.

Brian C. Trinque et al., J. Vac. Sci. Technol (2002) 531–536 "Recent advances in resists for 157 nm microlithography".

Francis W. Michelotti and J. H. Carter, J.Am. Chem. Soc. (1965) 224–233 "Polymerization of Norbomene and Derivatives. II. Selectivity in the Polymerization of Exoisomers by Iridium Catalysis".

Tran, H. et al. Daniel p. Snaders, Eric F. Connor, and Robert H. Grubbs, Macromolecules 2002, vol. 35, 6539–6549 American Chemical Society, "Metal–Catalyzed Vinyl Addition Polymers for 157 nm Resist Applications. 2. Fluorinated Norbornenes: Synthesis, Polymerization, and Initial Imaging Results".

Ralph R. Dammel et al., Journal of Photopolymer Science and Technology, vol. 14 (2001) 603–612 "New Resin Systems for 157 nm Lithography".

*Primary Examiner*—Rosemary Ashton

(57) ABSTRACT

There is disclosed a composition comprising a mixture of endo– and exo-2-(bicyclo[2.2.1]hept-5-en-2-yl)-2,2-fluoroalkyl-ethan-2-ol which is rich in the exo isomer, preferably the endo/exo concentration ratio is no greater than 5/95. The composition is useful for forming a repeat unit of a polymer which polymer may further comprise additional repeat units derived-from tert-butyl acrylate, hydroxyadamantyl acrylate, protected or unprotected fluorinated-olefins, 2-methyl-2-adamantyl acrylate, 2-propenoic acid, 2-hydroxy-1,1,2-trimethylpropyl ester. Polymers of this invention are useful as the binder component of a photoresist composition for microlithography.

51 Claims, No Drawings

PREPARATION AND USE OF EXO-2-FLUOROALKYL(BICYCLO[2.2.1]HEPT-5-ENES)

FIELD OF THE INVENTION

This invention relates to a monomer composition, a method for preparing the monomer composition and a polymer prepared therefrom. Polymers derived from the monomer composition are particularly suitable for use in a photoresist composition especially in the wavelength range shorter than 240 nm.

BACKGROUND OF THE INVENTION

In US 2002/0102490 of Ito et al., a process for synthesizing 3-(bicyclo[2.2.1]hept-5-en-2-yl)-1,1,1-trifluoro-2-(trifluoromethyl)propan-2-ol by reaction of cyclopentadiene with 1,1,1 trifluoro-2-trifluoromethyl-4-penten-2-ol complex is described. The monomer mixture resulting from that synthesis has an endo/exo isomer ratio of 80/20. Ito et al. is silent on synthesizing 3-(bicyclo[2.2.1]hept-5-en-2-yl)-1,1,1-trifluoro-2-(trifluoromethyl)propan-2-ol which is rich in the exo isomer. Ito et al. further discloses polymerizing 3-(bicyclo[2.2.1]hept-5-en-2-yl)-1,1,1-trifluoro-2-(trifluoromethyl)propan-2-ol with fluorinated olefins. Ito et al in "Synthesis and evaluation of alicyclic backbone polymers for 193 nm lithography" ACS Symposium Series (1998), 706 Micro- and Nanopatterning Polymers 208–223, American Chemical Society, discloses that radical polymerization of 3-(bicyclo[2.2.1]hept-5-en-2-yl)-1,1,1-trifluoro-2-(trifluoromethyl)propan-2-ol in the absence of catalyst is in general a very slow process thus to achieve reasonable addition polymerization rates of substituted norbornenes, metal based catalysts have been employed. Ito et al. identified certain comonomers, such as $SO_2$, which would increase the rate of polymerization. This very limited number of comonomers appear to enhance the rate of polymerization. However, the foregoing approaches have drawbacks. Metal based catalysts leave residues which are highly undesirable for use in short wavelength photolithographic applications; and, the use of comonomers, such as $SO_2$, degrade the transparency of the polymer at 157 nm. According to the Ito et al. publication the presence of $SO_2$ also decreases thermal stability of the polymer.

Polymers used in photoresist compositions must be highly transparent, highly free of contamination, particularly metallic contamination, must be processible according to the methods employed in the art, and, of course, must be cost effective. Because of the potential for even minute metallic residues to contaminate nano-scale circuitry, it is highly desirable to prepare polymers for use in photoresist compositions without resort to metal catalysis.

SUMMARY OF THE INVENTION

This invention relates to a composition comprising endo- and exo-2-(bicyclo[2.2.1]hept-5-en-2-yl)-2,2-fluoroalkyl-ethan-2-ol whereof the endo/exo concentration ratio is no greater than 5/95, as represented by the structure (I)

wherein the $R_f$ and $R_{f'}$ groups are the same or different fluoroalkyl groups of from 1 to about 10 carbon atoms, or taken together in cyclic form are $(CF_2)_n$ where n is an integer from 2 to 10.

This invention also relates to a polymer comprising about 10 mol % to about 60 mole % of a repeat unit derived from a composition comprising endo and exo monomer units represented by structure (II)

wherein the $R_f$ and $R_{f'}$ groups are the same or different fluoroalkyl groups of from 1 to 10 carbon atoms, or taken together in cyclic form are $(CF_2)_n$; n is an integer from 2 to 10; the monomer units of the composition having an endo/exo ratio no greater than 5/95.

This invention still further relates to a process for preparing a composition comprising endo- and exo-2-bicyclo[2.2.1]hept-5-en-2-yl)-2,2-fluoroalkyl-ethan-2-ol whereof the endo/exo concentration ratio is no greater than about 5/95, the process, comprising the steps of:

contacting in the presence of a source of free radicals a substituted norbornene with $ICH_2C(R_f)(R_{f'})OH$; wherein said substituted norbornene is represented by the structure (III)

to form an iodine-containing substituted norbornane compound represented by structure (IV);

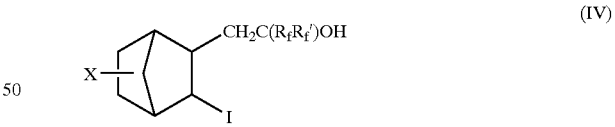

contacting said iodine-containing compound with a reducing agent to form a substituted norbornane represented by structure (V);

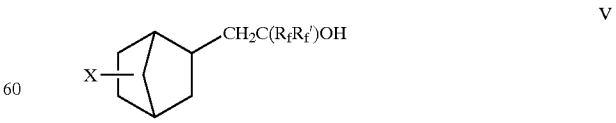

forming an olefin from the substituted norbornane (V) to form a composition comprising endo and exo 2-(bicyclo[2.2.1]hept-5-en-2-yl)-2,2-perfluoroalkyl-ethan-2-ol, whereof the endo/exo concentration ratio is no greater than 5/95 as represented by the structure (I).

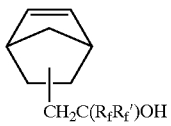
(I)

CH$_2$C(R$_f$R$_f$')OH wherein in the foregoing structures the R$_f$ and R$_f'$ groups are the same or different fluoroalkyl groups of from 1 to 10 carbon atoms, or taken together in cyclic form are (CF$_2$)$_n$, n is an integer from 2 to 10, and wherein X is selected from the group consisting of Cl, Br, and R$_8$SO$_2$—O—, where R$_8$ is an alkyl-, fluoroalkyl, aryl or fluoroaryl radical.

A photoresist suitable for use in the preparation of electronic circuits said photoresist comprising a photoactive agent and a polymer comprising 10 mol-% to 60 mol-% of A repeat unit represented by the structure (II)

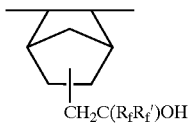
(II)

CH$_2$C(R$_f$R$_f$')OH and whereof said repeat unit is derived from a composition comprising endo- and exo-2-(bicyclo[2.2.1]hept-5-en-2-yl)-2,2-fluoroalkyl-ethan-2-ol, as represented by the structure (I)

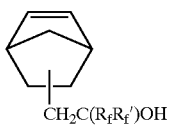
(I)

CH$_2$C(R$_f$R$_f$')OH wherein the R$_f$ and R$_f'$ groups are the same or different fluoroalkyl groups of from 1 to about 10 carbon atoms, or taken together in cyclic form are (CF$_2$)$_n$ where n is an integer from 2 to 10, whereof the endo/exo ratio is no greater than 5/95.

In a yet further aspect, this invention relates to an article comprising a semiconducting substrate having a surface, and a photoresist film disposed upon at least a portion of said surface, said photoresist film comprising a photoactive agent and a polymer comprising 10 mol-% to 60 mol-% of a repeat unit represented by the structure (II)

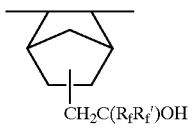
(II)

CH$_2$C(R$_f$R$_f$')OH and whereof said repeat unit is derived from a composition comprising endo- and exo-2-(bicyclo[2.2.1]hept-5-en-2-yl)-2,2-fluoroalkyl-ethan-2-ol, as represented by the structure (I)

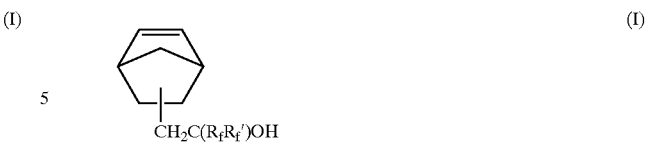
(I)

CH$_2$C(R$_f$R$_f$')OH wherein the R$_f$ and R$_f'$ groups are the same or different fluoroalkyl groups of from 1 to about 10 carbon atoms, or taken together in cyclic form are (CF$_2$)$_n$ where n is an integer from 2 to 10, whereof the endo/exo ratio is no greater than 5/95.

A process for preparing a patterned article the process comprising: forming a target surface by disposing upon a semiconducting substrate a photoresist film comprising a photoactive agent and a polymer comprising 10 mol-% to 60 mol-% of repeat units represented by the structure (II)

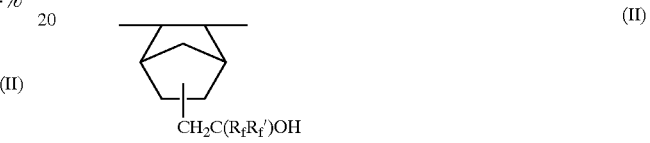
(II)

CH$_2$C(R$_f$R$_f$')OH whereof said repeat units are derived from a composition comprising endo- and exo-2-(bicyclo[2.2.1]hept-5-en-2-yl)-2,2-fluoroalkyl-ethan-2-ol, as represented by the structure (I)

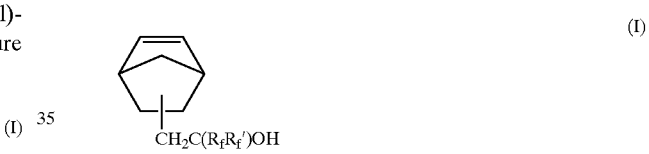
(I)

CH$_2$C(R$_f$R$_f$')OH wherein the R$_f$ and R$_f'$ groups are the same or different fluoroalkyl groups of from 1 to about 10 carbon atoms, or taken together in cyclic form are (CF$_2$)$_n$ where n is an integer from 2 to 10, whereof the endo/exo ratio is no greater than 5/95; illuminating said target surface in such a manner as to form a pattern of shadowed and illuminated areas, the illuminating step causing a change in solubility of said polymer; removing the soluble portions of said polymer, thereby producing a patterned article.

DETAILED DISCUSSION OF THE INVENTION

The present invention is directed to a composition of exo-rich 1-(bicyclo[2.2.1]hept-5-en-2-yl)-2,2-fluoroalkyl-ethan-2-ol, a method for preparing said composition, a polymer comprising repeat units derived from said composition and methods of synthesizing such composition.

The invention relates to a composition of 1-(bicyclo[2.2.1]hept-5-en-2-yl)-2,2-fluoroalkyl-ethan-2-ol with a high preponderance of the exo isomer. The as-synthesized composition is rich in exo isomer. A high preponderance of exo isomer is typically no greater than an endo/exo concentration of about 5/95, preferably no greater than 5/95.

The invention also relates to the discovery that the exo-rich 1-(bicyclo[2.2.1]hept-5-en-2-yl)-2,2-fluoroalkyl-ethan-2-ol of the invention copolymerizes by free-radical addition to higher yield than does a composition containing an 80/20 endo/exo ratio. The free radical addition polymerization is preferably conducted in the absence of metal catalyst. In particular, a copolymer of exo-rich 1-(bicyclo[2.2.1]hept-5- en-2-yl)-2,2-fluoroalkyl-ethan-2-ol with a halogenated, preferably fluorinated, α-unsaturated olefinic comonomer, preferably tetrafluoroethylene, is formed in higher yields than the 80/20 endo/exo mixture. Free-radical addition, in the absence of a metal catalyst, of a composition comprising exo-rich 1-(bicyclo[2.2.1]hept-5-en-2-yl)-2,2-fluoroalkyl-ethan-2-ol can achieve a three-fold yield increase.

Further, polymers derived from the exo-rich 1-(bicyclo[2.2.1]hept-5-en-2-yl)-2,2-fluoroalkyl-ethan-2-ol are characterized by surprisingly high incorporation of repeat units derived from the 1-(bicyclo[2.2.1]hept-5en-2-yl)-2,2-fluoroalkyl-ethan-2-ol monomer.

Polymers derived from the exo-rich 1-(bicyclo[2.2.1]hept-5-en-2-yl)-2,2-fluoroalkyl-ethan-2-ol also have very high transparency. Because of its transparency properties the polymer can be useful in a variety of optical applications such as photoresists, optical waveguides, optical elements such as lenses, pellicles, beam splitters, diffraction gratings, or optical couplets.

Thus, in one embodiment, the invention relates to a photoresist composition comprising a polymer derived from 1-(bicyclo[2.2.1]hept-5-en-2-yl)-2,2-fluoroalkyl-ethan-2-ol, an article comprising a semiconducting substrate with a photoresist comprising a polymer derived from 1-(bicyclo[2.2.1]hept-5-en-2-yl)-2,2-fluoroalkyl-ethan-2-ol disposed upon at least a portion thereof and processes for preparing the article and patterning the article.

In one embodiment of the invention there is provided a substituted norbornene composition comprising a mixture of endo- and exo-1-(bicyclo[2.2.1]hept-5-en-2-yl)-2,2-fluoroalkyl-ethan-2-ol whereof the endo/exo concentration ratio is no greater than 5/95. The 1-(bicyclo[2.2.1]hept-5-en-2-yl)-2,2-fluoroalkyl-ethan-2-ol, is represented by the structure (I)

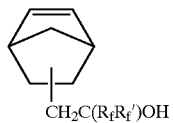

CH$_2$C(R$_f$R$_f$')OH (I)

wherein the R$_f$ and R$_f$' groups are the same or different fluoroalkyl groups of from 1 to 10 carbon atoms, or taken together in cyclic form are (CF$_2$)$_n$ where n is an integer from 2 to 10. Either or both of R$_f$ and R$_f$' can be partially fluorinated alkyl groups or fully fluorinated alkyl groups (i.e., perfluoroalkyl groups). Preferably R$_f$ and R$_f$' are perfluoromethyl or perfluoroethyl. Most preferably, R$_f$ and R$_f$' are perfluoromethyl.

For purposes of the present invention the term "taken together in cyclic form" means that the R$_f$ and R$_f$' groups are not separate, discrete fluorinated alkyl groups, but that together they form a ring structure. One embodiment of such ring structure is illustrated by, but not limited to, the 5-membered ring:

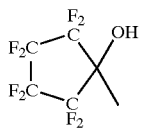

One of skill in the art will appreciate that numerous other embodiments of ring structures are also encompassed in the present invention.

In one embodiment of the invention, the exo-rich 1-(bicyclo[2.2.1]hept-5-en-2-yl)-2,2-fluoroalkyl-ethan-2-ol composition can be polymerized in the absence of a different comonomer in the presence of a metal catalyst.

Alternatively, the exo-rich 1-(bicyclo[2.2.1]hept-5-en-2-yl)-2,2-fluoroalkyl-ethan-2-ol composition can be polymerized with one or more different monomers, preferably by free radical addition which avoids the need for metal catalysts.

In a further embodiment of the present invention a polymer can comprise 10 mol-% to 60 mol-% of repeat units represented by the structure (II)

(II)

CH$_2$C(R$_f$R$_f$')OH wherein the R$_f$ and R$_f$' groups are the same or different fluoroalkyl groups of from 1 to 10 carbon atoms typically 1 to 5 carbon atoms, or taken together in cyclic form are (CF$_2$)$_n$ where n is an integer from 2 to 10, the polymer being derived from exo-rich 1-(bicyclo[2.2.1]hept-5-en-2-yl)-2,2-fluoroalkyl-ethan-2-ol. Preferably R$_f$ is perfluoromethyl or perfluoroethyl. Most preferably R$_f$ is perfluoromethyl. The polymer can contain up to about 90 mol-%, preferably about 40 to about 90% of units derived from one or more different monomers.

Different monomers that can be incorporated into the polymer can be derived from one or more olefins which may contain one or more heteroatoms. Typically such olefins contain from about 2 to about 20 carbon atoms. Suitable heteroatoms include, without limit, halogen atoms, oxygen atoms, and nitrogen atoms. The olefin may be straight chain or branched chain and may contain one or more single-ring or multi-ring saturated or unsaturated hydrocarbon groups which may also contain one or more heteroatom substituents such as oxygen, halogen, and nitrogen. When the monomer comprises a single ring or multi ring group such cyclic group can contain from 3 to 18 carbon atoms. Examples of cyclic groups include norbornyl, adamantyl, 2-methyl-2-adamantyl, isobornyl and the like. When the monomer comprises a heteroatom it may contain one or more halogen atoms, carboxylic groups, hydroxyl groups, ester groups, carbonyl groups and carboxyl groups, ether groups, amide groups and nitrile groups.

In one embodiment of the invention the polymer is derived from the monomer represented by structure (I) and at least one halogenated olefin, specifically, a fluoroolefin having at least one fluorine atom attached to an ethylenically unsaturated carbon. The fluoroolefin can comprise from 2 to about 20 carbon atoms. Preferred fluoroolefins include tetrafluoroethylene, hexafluoropropylene, chlorotrifluoroethylene, vinylidene fluoride, vinyl fluoride, perfluoro-(2,2-dimethyl-1,3-dioxole), perfluoro-(2-methylene4-methyl-1,3-dioxolane), CF$_2$=CFO(CF$_2$)$_t$CF=CF$_2$, where t is 1 or 2, and R$_f$"OCF=CF$_2$ wherein R$_f$" is a fluoroalkyl group of from 1 to about 10 carbon atoms. Most preferred is tetrafluoroethylene.

The polymer can further comprise one or more units which provide useful functionality in photolithographic applications. Such functionality is imparted by chemical groups that promote or facilitate adhesion to the substrate, etch resistance, developability, high contrast, high process latitude, and low line edge roughness.

In one embodiment of this invention, the polymer contains one or more protected acidic groups that yield a carboxylic acid as the hydrophilic group upon exposure to photogenerated acid. Such protected acidic groups include, but are not limited to, A) esters capable of forming, or rearranging to, a tertiary cation, B) esters of lactone, C) acetal esters, D) β-cyclic ketone esters, E) α-cyclic ether esters, and F) MEEMA (methoxy ethoxy ethyl methacrylate) and other esters which are easily hydrolyzable because of anchimeric assistance. Some specific examples in category A) are t-butyl ester, 2-methyl-2-adamantyl ester, and isobornyl ester.

Polymer derived from the exo-rich 1-(bicyclo[2.2.1]hept-5-en-2-yl)-2,2-fluoroalkyl-ethan-2-ol preferably comprise one or more components having protected acidic fluorinated alcohol groups (e.g., —C($R_f$)($R_f'$)O$R_a$, where $R_a$ is not H) and/or other acidic groups that can yield hydrophilic groups by the reaction with acids or bases generated photolytically such as from photoactive compounds (PACs). A protected fluorinated alcohol group contains a group that protects the fluorinated alcohol group from exhibiting its acidity while in this protected form. A protecting group ($R_a$) is normally chosen on the basis of its being acid-labile, such that when acid is produced upon imagewise exposure, it will catalyze deprotection of the protected acidic fluorinated alcohol groups and/or other protected acidic groups and production of hydrophilic acidic groups that are necessary for development under aqueous conditions. In addition, the fluorine-containing copolymers may also contain acid functionality that is not protected (e.g., —C($R_f$)($R_f'$)O$R_a$, where $R_a$=H).

As one illustrative example, when the tertiary-butyl group is the protecting group in a tertiary-butyl ester and this protecting group protects the free acid. In undergoing deprotection (conversion of protected acid to free acid), the ester is converted to the corresponding acid.

An alpha-alkoxyalkyl ether group (i.e., $R_a$=O$R_b$, $R_b$=$C_1$–$C_{11}$, alkyl) is a preferred protecting group for the fluoroalcohol group because it has been found to provide a high degree of transparency in the photoresist composition. An illustrative, but non-limiting, example of an alpha-alkoxyalkyl ether group that is effective as a protecting group, is methoxy methyl ether (MOM). A protected fluoroalcohol with this particular protecting group can be obtained by reaction of chloromethylmethyl ether with the fluoroalcohol. An especially preferred protected fluoroalcohol group has the structure:

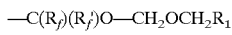

—C($R_f$)($R_f'$)O—CH$_2$OCH$_2$R$_1$ wherein, $R_f$ and $R_f'$ are the same or different fluoroalkyl groups of from 1 to 10 carbon atoms or taken together in cyclic form (CF$_2$)$_n$ wherein n is 2 to 10; R, is H, a linear alkyl group of 1 to 10 carbon atoms, or a branched alkyl group of 3 to 10 carbon atoms.

The fluoroalcohol functional group (protected or unprotected) of this invention can be used alone or it can be used in combination with one or more other acidic groups, such as carboxylic acid functional group (unprotected) and t-butyl ester of carboxylic acid functional group (protected).

Carbonates formed from a fluorinated alcohol and a tertiary aliphatic alcohol can also be used as protected acidic fluorinated alcohol groups.

In one embodiment of the invention the polymer comprises a hydroxy ester group which serves as a protected acidic group. An example of a hydroxy ester group which may be incorporated into the polymer of this invention has the formula

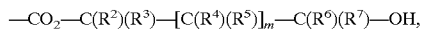

—CO$_2$—C(R$^2$)(R$^3$)—[C(R$^4$)(R$^5$)]$_m$—C(R$^6$)(R$^7$)—OH, wherein
m=0, 1, 2, 3, 4 or 5;
R$^2$, R$^3$=$C_1$–$C_6$ alkyl, $C_1$–$C_6$ alkyl substituted with an ether oxygen; or R$^2$ and R$^3$ taken together form a 3- to 8-membered ring, optionally substituted with an ether oxygen, provided that the carbon attached to R$^2$ and R$^3$ is not at a bridgehead position;
R$^4$, R$^5$=H, $C_1$–$C_6$ alkyl, $C_1$–$C_6$ alkyl substituted with an ether oxygen; or R$^4$ and R$^5$ taken together form a 3- to 8-membered ring, optionally substituted with an ether oxygen;
R$^6$, R$^7$=H, $C_1$–$C_6$ alkyl, or $C_1$–$C_6$ alkyl substituted with an ether oxygen; or R$^6$ and R$^7$ taken together form a 3- to 8-membered ring, optionally substituted with an ether oxygen; or R$^2$ and R$^6$ taken together with —[C(R$^4$)(R$^5$)]$_{m1}$— form a 4- to 8-membered ring, provided that the carbon attached to R$^2$ and R$^3$ is not at a bridgehead position.
In a preferred embodiment of this invention,
R$^2$, R$^3$=$C_1$–$C_6$ alkyl, or R$^2$ and R$^3$ taken together form a 5- or 6-membered ring, provided that the carbon attached to R$^1$ and R$^2$ is not at a bridgehead position;
R$^4$, R$^5$=H, $C_1$–$C_6$ alkyl, or R$^4$ and R$^5$ taken together form a 5- or 6-membered ring;
R$^6$, R$^7$=H, $C_1$–$C_6$ alkyl, or R$^6$ and R$^7$ taken together form a 5- or 6-membered ring; and
m$_1$=0, 1, 2 or 3.

The hydroxy ester group of the formula —CO$_2$—C(R$^2$)(R$^3$)—[C(R$^4$)(R$^5$)]$_m$—C(R$^6$)(R$^7$)—OH can be incorporated into polymers and copolymers by any of the several methods known to those skilled in the art. For example, acid-functionalized polymers can be reacted with a diol, HO—C(R$^2$)(R$^3$)—[C(R$^4$)(R$^5$)]$_m$—C(R$^6$)(R$^7$)—OH or an epoxide

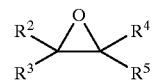

wherein $R_2$–$R_7$ are defined above to give the corresponding ester.

The hydroxy ester group of the present invention can be incorporated into an ethylenically unsaturated compound that is polymerized with other monomers, to form the desired hydroxy ester functionalized polymer. For example, the acrylate, H$_2$C=C(H)CO$_2$—C(R$^2$)(R$^3$)—[C(R$^4$)(R$^5$)]$_m$—C(R$^6$)(R$^7$)—OH, can be copolymerized.

Suitable hydroxy esters include 2-propenoic acid, 2-hydroxy-1,1,2-trimethylpropyl ester (PinAc) and the analogous methacrylate monomer (PinMAc), and the monoacrylate and mono-methacrylate derivatives of 2,5-dimethyl-2,5-hexanediol. Suitable hydroxy esters can also be prepared from the products of the reductive dimerization of a wide variety of aliphatic and cycloaliphatic ketones, such a cyclohexanone, cyclopentanone and methyl ethyl ketone. Suitable hydroxy esters and the method of synthesizing them are described in U.S. Provisional Application No. 60/415,855 filed on Oct. 3, 2002 which is incorporated herein by reference in its entirety.

In one embodiment, the polymer can comprise other esters. Acrylate comonomers that can be polymerized with the exo-rich 1-(bicyclo[2.2.1]hept-5-en-2-yl)-2,2- fluoroalkyl-ethan-2-ol include acrylic acid, methyl acrylate, ethyl acrylate, propyl acrylate, tert-butyl acrylate, 2-methyl-2-adamantyl acrylate, 2-methyl-2-norbornyl acrylate, 2-methoxyethyl acrylate, 2-hydroxyethyl acrylate, 2-cyanoethyl acrylate, glycidyl acrylate, and 2,2,2-trifluoroethyl acrylate, as well as the corresponding methacrylate monomers. Such acrylates, as well as methacrylates, can be polymerized together with the exo-rich 1-(bicyclo[2.2.1]hept-5-en-2-yl)-2,2-fluoroalkyl-ethan-2-ol and along with other ethylenically unsaturated compounds such as other fluoro-olefins and/or other polycyclic olefins.

In this invention, often, but not always, the components having protected groups are repeat units that have been incorporated in a copolymer that forms a component of a composition (as discussed above).

Frequently the protected acidic groups are present in one or more comonomers that are polymerized to form a given copolymer of this invention. Alternatively, in this invention, a copolymer can be formed by copolymerization with an acid-containing comonomer and then subsequently acid functionality in the resulting acid-containing copolymer can be partially or wholly converted by appropriate means to derivatives having protected acidic groups.

In a still further embodiment, the polymer can be a tetrapolymer formed by uniting four different monomers and each monomer, typically imparts a different functionality (adhesion to the substrate, etch resistance, developability) such that the tetrapolymer encompasses more than one functionality.

In a preferred embodiment, the invention comprises a terpolymer derived from the exo-rich 1-(bicyclo[2.2.1]hept-5-en-2-yl)-2,2-fluroalkyl-ethan-z-ol composition, an olefinic monomer having at least one fluorine atom attached to an olefinic carbon atom, and a tertiary alkyl acrylate. The tertiary alkyl acrylate provides protected acidic groups in the polymer which, when subjected to photogenerated acid, are converted to hydrophilic acidic groups for development of a resist coating.

In a first step of the process of the invention for making the exo-rich monomer composition, in the presence of a source of free radicals, an iodine substituted fluoroalcohol such as $ICH_2C(R_f)(R_{f'})OH$ where $R_f$ and $R_{f'}$ is defined above, is contacted with a substituted norbornene represented by the structure (III) hereinabove where X may be attached to either adjacent secondary carbons and X is a leaving group selected from the group consisting of Cl, F, Br, $R_8SO_2$—O—, wherein $R_8$ is an alkyl, fluoroalkyl aryl or fluoroaryl radical. Typically, the alkyl group contains from 1 to 20 carbon atoms and the aryl group contains from 3 to 20 carbon atoms. Preferably X is Cl and $R_f$ and $R_{f'}$ is perfluoromethyl. A suitable reaction temperature is employed which is typically above ambient (20–25° C.), more typically from about 50 to about 90° C.

$ICH_2C(R_fR_{f'})OH$ wherein $R_f$ and $R_{f'}$ are defined above, preferably $ICH_2C(CF_3)_2OH$, can be prepared by reaction of 47% hydroiodic acid with 2,2-bis(fluoroalkyl)oxirane, preferably 2,2-bis(trifluoromethyl)oxirane (for when $R_f$ and $R_{f'}$ is perfluoromethyl), according to the method of V. A. Petrov, Synthesis, No, 15, 2225, 2002.

In one embodiment, a mixture of endo and exo isomers of 5-chloronorbornene-2 is prepared by Diels-Alder reaction of vinyl chloride and dicyclopentadiene. Such a reaction is typically conducted at elevated temperatures. A reaction temperature of about 180° C. for a reaction time of about 12 hours was reported in Roberts et al, J. American Chem. Soc., 72 (1950), 3116. The product of this reaction is a mixture of exo and endo isomers but is predominantly endo, typically 80% endo.

In a more preferred embodiment of the process of the invention, exo-5-chloronorbornene-2 is prepared by low temperature addition of HCl to norbornadiene according to the method of L. Schmerling, J. P. Luvisi, W. Welch, JACS, 78, 2819. It is found surprisingly in the practice of the invention that when the exo-5-chloronorbornene is employed in preference to the endo/exo mixture, the addition reaction of $ICH_2C(CF_3)_2OH$ to the double bond of the composition represented by structure (III), wherein X chlorine, produces a higher yield of the composition represented by the structure (IV)

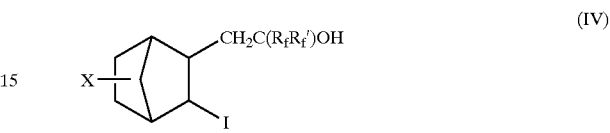

(IV)

In the next step, the C—I bond is reduced to a C—H bond. Any method by which this can be accomplished is suitable. Suitable methods include but are not limited to Zn reduction as described in Brace, J. Org. Chem. 27 (1962), 3027 ff and, catalytic reduction with a palladium catalyst as described in Brace, J. Fluorine Chem. 20 (1982) 313ff. More broadly, catalytic hydrogenolysis is also described in Augstine, Catalytic Hydrogenolysis, Marcel Dekker, New York (1965), 125–146.

Metal reduction of compounds represented by structure IV can be carried out using metals, such as Zn, Zn/Cu, or Fe in a suitable solvent at elevated temperatures, typically from about 30 to about 100° C., in the presence of one or more acids such as for example, hydroiodic, hydrobromic or hydrochloric.

Reduction of compounds represented by structure IV using hydrogen can also be carried out. An inert solvent is used, typically an aqueous solvent or an organic solvent (such as one or more of an alcohol, tetrahydrofuran, a glyme, etc.) in the presence of a hydrogenation catalyst (for example a Pd or Pt catalyst) and suitable base (sodium and potassium bicarbonates or carbonates, amines and the like) at an elevated temperature typically ranging from about 40 to about 100° C., preferably about 45 to about 100° C. The method based on use of hydrogen is preferred one, since that method avoids the formation of by-products. Hydrogen reduction is preferred when the exo-chloride is used, but either method is suitable when the endo/exo chloride is used.

Formation of olefins by elimination of HCl from an alkyl chloride is a known reaction, and may be conducted but is not limited to, according to the method of Bartsch et al, J. Org. Chem. 56, 212 (1991) using suitable strong base, such as potassium t-butoxide in solvents such as for example THF, diglyme or triglyme. In a preferred embodiment of the invention, the resulting product is a composition comprising a mixture of endo- and exo-2-(bicyclo[2.2.1]hept-5-en-2-yl)-2,2-perfluoroalkyl-ethan-2-ol whereof the endo/exo concentration ratio is no greater than 5/95, whereof the exo portion is represented by the structure (VI)

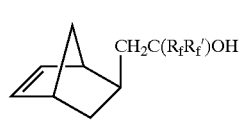

VI wherein the $R_f$ and $R_{f'}$ groups are the same or different fluoroalkyl groups of from 1 to 10 carbon atoms, or taken together in cyclic form are $(CF_2)_n$ where n is an integer from 2 to 10, preferably perfluoromethyl or perfluoroethyl, most preferably perfluoromethyl.

The olefinically unsaturated composition represented by structure (I) or in a preferred embodiment, the olefinically unsaturated composition represented by structure (VI), wherein $R_f$ and $R_{f'}$ is trifluoromethyl, may be contacted with a source of free radicals in the presence of a fluoroolefin and caused to polymerize to form the polymer of the invention comprising repeat units represented by the structure (II). Suitable sources of free radicals included peroxy compounds, such as bis(4-tert-butylcyclohexyl) peroxydicarbonate and $CF_3CF_2CF_2OCF(CF_3)CO_2O_2CCF(CF_3)OCF_2CF_2CF_3$, and azo compounds, such as azo-bis-isobutyronitrile. Polymerization temperatures are generally selected in accord with the half-life of the free radical source and are typically in the range of about 0° C. to about 200° C., more preferably in the range of about 40° C. to about 100° C.

Polymerizations are preferably conducted in a closed reaction vessel to minimize loss of volatile reagents and in the absence of oxygen. Polymerizations may be conducted without solvent when the mixture of monomers forms a liquid phase or in the presence of solvent. Solvents are generally chosen to avoid undesirable chain transfer during the course of polymerization. Suitable solvents include chlorofluorocarbons, such as 1,1,1-trichlorotrifluoroethane, hydrofluorocarbons, such as 1,1,1,3,3-pentafluorobutane, esters, such as methyl acetate and ethyl acetate, and tertiary alkyl alcohols, such as tert-butanol.

Polymerizations may be conducted in a batch mode, that is, all reagents are added to the reaction vessel which is then heated to the desired polymerization temperature. More preferably, polymerizations may be conducted in a semi-batch mode in which portions of the monomers and solvent are added to the reaction vessel and are brought to polymerization temperature. The remaining monomers, solvent and free radical source are then fed to the reaction vessel so as to cause polymerization. A continuous process may also be employed in which monomers, solvent and free radical source are fed to a reaction vessel and a reactor stream containing the desired product is removed throughout the process.

Preferably the exo-rich monomer composition of this invention is used in the polymerization; however, a monomer composition with a reduced exo content may be employed by adding to the polymerization feed a conventional higher endo content composition such as the kind described in US 2002/0102490 of Ito et al.

The polymers of this invention can be used as the binder of a photoresist composition by combining one or more polymers described herein with at least one photoactive component (PAC) such as are well-known in the art. A PAC is a compound that typically affords either acid or base upon exposure to actinic radiation. If an acid is produced upon exposure to actinic radiation, the PAC is termed a photoacid generator (PAG). If a base is produced upon exposure to actinic radiation, the PAC is termed a photobase generator (PBG). Several suitable photoacid generators are disclosed in WO 00/66575.

A PAG (photoacid generator) is a preferred subset of PAC (photoactive components). Suitable photoacid generators for this invention include, but are not limited to, 1) sulfonium salts (structure XI), 2) iodonium salts (structure XII), and 3) hydroxamic acid esters, such as structure XIII.

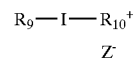

XII

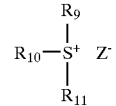

XI

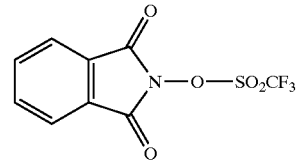

XIII

In structures XI and XII, $R_9$–$R_{11}$ are independently substituted or unsubstituted $C_6$–$C_{20}$ aryl or substituted or unsubstituted $C_7$–$C_{40}$ alkylaryl or aralkyl. Representative aryl groups include, but are not limited to, phenyl, naphthyl and anthracenyl. Suitable substituents include, but are not limited to, one or more oxygen, nitrogen, halogen, or sulfur atoms. When the heteroatom is oxygen the substituent can contain hydroxyl (—OH) and $C_1$–$C_{20}$ alkyloxy (e.g., $C_{10}H_{21}O$. The anion Z- in structures I–II can be, but is not limited to, $SbF_6$— (hexafluoroantimonate), $CF_3SO_3$— (trifluoromethylsulfonate=triflate), and $C_4F_9SO_3$— (perfluorobutylsulfonate). A typical PAG is triphenylsulfonium nonaflate.

Dissolution Inhibitors and Additives

Various dissolution inhibitors can be utilized in this invention. Ideally, dissolution inhibitors (DIs) for far and extreme UV resists (e.g., 193 nm resists) should be designed/chosen to satisfy multiple materials needs including dissolution inhibition, plasma etch resistance, and adhesion behavior of resist compositions comprising a given DI additive. Some dissolution inhibiting compounds also serve as plasticizers in resist compositions.

A variety of bile-salt esters (i.e., cholate esters) are particularly useful as DIs in the compositions of this invention. Bile-salt esters are known to be effective dissolution inhibitors for deep UV resists, beginning with work by Reichmanis et al. in 1983. (E. Reichmanis et al., "The Effect of Substituents on the Photosensitivity of 2-Nitrobenzyl Ester Deep UV Resists", *J. Electrochem. Soc.* 1983, 130, 1433–1437.) Bile-salt esters are particularly attractive choices as DIs for several reasons, including their availability from natural sources, their high alicyclic carbon content, and particularly for their transparency in the deep and vacuum UV region, (which essentially is also the far and extreme UV region), of the electromagnetic spectrum. Typically, they are highly transparent at 193 nm. Furthermore, the bile-salt esters are also attractive DI choices since they may be designed to have widely ranging hydrophobic to hydrophilic compatibilities depending upon hydroxyl substitution and functionalization.

Representative bile-acids and bile-acid derivatives that are suitable as additives and/or dissolution inhibitors for this invention include, but are not limited to cholic acid, deoxycholic acid, lithocholic acid, t-butyl deoxycholate, t-butyl lithocholate, and t-butyl-3-α-acetyl lithocholate.

The invention is not limited to use of bile-acid esters and related compounds as dissolution inhibitors. Other types of dissolution inhibitors, such as various diazonaphthoquinones (DNQs) and diazocoumarins(DCs), can be utilized in this invention in some applications. Diazanaphthoquinones and diazocoumarins are generally suitable in resists compositions designed for imaging at higher wavelengths of UV light (e.g., 365 nm and perhaps at 248 nm). These dissolution inhibitors are generally not preferred in resist compositions designed for imaging with UV light at 193 nm or lower wavelengths, since these compounds absorb strongly in this region of the UV and are usually not sufficiently transparent for most applications at these low UV wavelengths.

The photoresist compositions of this invention can contain optional additional components together with the binder and the photoactive agent. Examples of additional components which can be added include, but are not limited to, one or more of resolution enhancers, adhesion promoters, crosslinking agents, residue reducers, coating aids, plasticizers, solvents and $T_g$ (glass transition temperature) modifiers. Suitable solvents are typically organic such as 2-heptanone, propylene glycol methyl ether acetate and trichlorobenzene.

Solvents

Photoresists of this invention are prepared as coating compositions by dissolving the components of the photoresist in a suitable solvent, for example, ether esters such as propyleneglycol monomethyl ether acetate, 2-ethoxyethyl acetate, 2-methoxyethyl acetate, and ethyl 3-ethoxypropionate; ketones such as cyclohexanone, 2-heptanone, and methyl ethyl ketone; esters such as butyl acetate, ethyl lactate, methyl lactate, and ethyl acetate; glycol ethers such as propylene glycol monomethyl ether, ethylene glycol monomethyl ether, ethyleneglycol monoethyl ether, and 2-methoxyethyl ether (diglyme); unsubstituted and substituted hydrocarbons and aromatic hydrocarbons such as hexane, toluene, and chlorobenzene; and fluorinated solvents such as CFC-113 (1,1,2-trichlorotrifluoromethane, E. I. du Pont de Nemours and Company), and 1,2-bis(1,1,2,2-tetrafluoroethoxy)ethane. High boiling solvents can be added, for example, xylene or other unsubstituted or substituted aromatic hydrocarbons; ethers such as benzyl ethyl ether, and dihexyl ether; glycol ethers such as diethyleneglycol monomethyl ether, and diethyleneglycol monoethyl ether; ketones such as acetonylacetone, and isophorone; alcohols such as 1-octanol, 1-nonanol, and benzylalcohol; esters such as benzyl acetate, ethyl benzoate, diethyl oxalate, diethyl maleate, ethylene carbonate, and propylene carbonate; and lactones such as γ-butyrolactone and δ-valerolactone. Alternatively, supercritical $CO_2$ may be useful as a solvent. These solvents may be used alone or in admixture of two or more. Typically, the solids content of the photoresist varies between 5 and 50 percent by weight of the total weight of the photoresist composition.

Imagewise Exposure

The photoresist compositions of this invention are sensitive in the ultraviolet region of the electromagnetic spectrum and especially to those wavelengths greater than or equal to 365 nm. Imagewise exposure of the resist compositions of this invention can be done at many different UV wavelengths including, but not limited to, 365 nm, 248 nm, 193 nm, 157 nm, and lower wavelengths. Imagewise exposure is preferably done with ultraviolet light of 248 nm, 193 nm, 157 nm, or lower wavelengths; is more preferably done with ultraviolet light of 193 nm, 157 nm, or lower wavelengths; and is still more preferably done with ultraviolet light of 157 nm or lower wavelengths. Imagewise exposure can either be done digitally with a laser or equivalent device or non-digitally with use of a photomask. Suitable laser devices for digital imaging of the compositions of this invention include, but are not limited to, an argon-fluorine excimer laser with UV output at 193 nm, a krypton-fluorine excimer laser with UV output at 248 nm, and a fluorine (F2) laser with output at 157 nm. Since, as discussed supra, use of UV light of lower wavelength for imagewise exposure corresponds to higher resolution (lower resolution limit), the use of a lower wavelength (e.g., 193 nm or 157 nm or lower) is generally preferred over use of a higher wavelength (e.g., 248 nm or higher).

Development

The photoresists derived from the polymers of this invention can either be positive- or negative-working photoresists, depending upon choice of components in the fluoropolymer, the presence or absence of optional dissolution inhibitor and crosslinking agents, and the choice of solvent used in development.

In positive-working photoresists, the polymer becomes more soluble and/or dispersible in a solvent used in development in the imaged or irradiated areas whereas in a negative-working photoresist, the polymer becomes less soluble and/or dispersible in the imaged or irradiated areas. In one preferred embodiment of this invention, irradiation causes the generation of acid or base by the photoactive component. The acid or base may catalyze removal of protecting groups from the polymer, for example from the fluoroalcohol or other acidic groups present in the polymer.

Development in an aqueous base such a tetramethylammonium hydroxide would result in the formation of appositive image whereas development in an organic solvent or critical fluid (having moderate to low polarity), would result in a negative-working system in which exposed areas remain and unexposed areas are removed. Positive-working photoresists are preferred.

A variety of different crosslinking agents can be employed in the photoresist composition as required or optional photoactive component(s) in the negative-working mode of this invention. (A crosslinking agent is required in embodiments that involve insolubilization in developer solution as a result of crosslinking, but is optional in preferred embodiments that involve insolubilization in developer solution as a result of polar groups being formed in exposed areas that are insoluble in organic solvents and critical fluids having moderate/low polarity). Suitable crosslinking agents include, but are not limited to, various bis-azides, such as 4,4'-diazidodiphenyl sulfide and 3,3'-diazidodiphenyl sulfone. Preferably, a negative-working resist composition containing a crosslinking agent(s) also contains suitable functionality (e.g., unsaturated C=C bonds) that can react with the reactive species (e.g., nitrenes) that are generated upon exposure to UV to produce crosslinked polymers that are not soluble, dispersed, or substantially swollen in developer solution, which consequently imparts negative-working characteristics to the composition.

The fluorine-containing polymers of this invention when used as the binder of a resist composition must contain sufficient functionality for development following imagewise exposure to UV light. Preferably, the functionality is acid or protected acid such that aqueous development is possible using a basic developer such as sodium hydroxide solution, potassium hydroxide solution, or ammonium hydroxide solution. Typically, the level of acidic groups, typically furnished by an acidic fluralcohol, can be determined for a given composition by optimizing the amount needed for good development in aqueous alkaline developer.

When an aqueous processable photoresist is coated or otherwise applied to a substrate and imagewise exposed to UV light, development of the photoresist composition may require that the polymer used as the binder component contain sufficient acidic groups (e.g., fluoroalcohol groups) and/or protected acidic groups that are at least partially deprotected upon exposure to render the photoresist (or other photoimageable coating composition) processable in aqueous alkaline developer. In case of a positive-working photoresist layer, the photoresist layer will be removed during development in portions which are exposed to UV radiation but will be substantially unaffected in unexposed portions during development by aqueous alkaline liquids such as wholly aqueous solutions containing 0.262 N tetramethylammonium hydroxide (with development at 25° C. usually for less than or equal to 120 seconds). In case of a negative-working photoresist layer, the photoresist layer will be removed during development in portions which are unexposed to UV radiation but will be substantially unaffected in exposed portions during 35 development using either a critical fluid or an organic solvent.

A critical fluid, as used herein, is one or more substances heated to a temperature near or above its critical temperature and compressed to a pressure near or above its critical pressure. Critical fluids in this invention are at least at a temperature that is higher than 15° C. below the critical temperature of the fluid and are at least at a pressure higher than atmospheres below the critical pressure of the fluid. Carbon dioxide may be used for the critical fluid in the present invention. Various organic solvents can also be used as developer in this invention. These include, but are not limited to, halogenated solvents and non-halogenated solvents. Halogenated solvents are preferred and fluorinated solvents are more preferred.

The substrate employed in this invention can illustratively be silicon, silicon oxide, silicon nitride, or various other materials used in semiconductive manufacture.

In a further embodiment of the invention is provided an article comprising a semi-conducting substrate having a surface, and a photoresist film disposed upon at least a portion of said surface, said photoresist film comprising a photoactive group and a polymer as described herein.

Preferably said semi-conducting substrate is silicon. The photoresist film disposed thereupon may be so disposed by any convenient method. Spin-coating a solution is a particularly attractive method for casting thin uniform polymeric films upon a substrate. The photoresist film thickness is typically in the range of about 50 nm to about 500 nm.

In a further embodiment of the present invention is provided a process for preparing a patterned article by photolithography, the process comprising:

forming a target surface by disposing upon a semiconducting substrate a photoresist film comprising a photoactive group and a polymer as described hereinabove, forming a pattern of shadowed and illuminated areas on a target surface by illuminating the target surface followed by an optional heating step, said illuminating and optional heating being sufficient to change the solubility of said polymer;

forming a patterned article by removing the soluble portions of said polymer, thereby producing a patterned article.

Preferably the target surface is illuminated by exposure to a light source. The light source can be in the vacuum ultra-violet, having a wavelength range of 140 nm to 260 nm. Most preferably the light is a source in the VUV having a wavelength in the range of 140 to 200 nm.

One of skill in the art will appreciate that once the patterned article of the invention is prepared according to the process hereof, or any alternative process such as is known in the art, additional processing steps may be conducted directed at the fabrication of an electronic circuit. Such additional processing steps may include chemical or ion-beam etching, metallization, doping and other processes known in the art, and combinations thereof.

The present invention is further described in the following examples.

EXAMPLES

Materials $ICH_2C(CF_3)_2OH$ was prepared by the reaction of 47% hydroiodic acid with 2,2-bis(trifluoromethyl)oxirane (supplied by E. I. DuPont de Nemours and Company) according to the method in V. A. Petrov, *Synthesis*, 15, 2225, (2002). A mixture of endo-exo isomers of 5-chloronorbomene-2 was prepared by Diels-Alder reaction of vinyl chloride and dicyclopentadiene (supplied by Aldrich) at 180° C., for 12 h.

Predominantly exo-5-chloronorbornene-2 was prepared by low temperature addition of HCl to norbornadiene according to the method of L. Schmerling, J. P. Luvisi, W. Welch, *JACS*, 78 (1956) 2819. Material prepared by this method contained 25% of nortricyclyl chloride and was used without purification. The inventors hereof believe that nortricyclyl chloride is not active under radical conditions.

Dry THF (supplied by Aldrich 99.9%, water 0.005%) and diglyme (supplied by Aldrich 99.9%, water 0.005%) and potassium t-butoxide (supplied by Aldrich, 95%), norbornadiene (supplied by Acros, 96%) were purchased from commercial sources and used without further purification.

| GLOSSARY | |
|---|---|
| Analytical/Measurements | |
| bs | broad singlet |
| $\delta$ | NMR chemical shift measured in the indicated solvent |
| g | gram |
| h | hours |
| NMR | Nuclear Magnetic Resonance |
| $^1$H NMR | Proton NMR |
| $^{13}$C NMR | Carbon-13 NMR |
| $^{19}$F NMR | Fluorine-19 NMR |
| s | singlet |
| sec. | second(s) |
| m | multiplet |
| mL | milliliter(s) |
| mm | millimeter(s) |
| $T_g$ | Glass Transition Temperature |
| $M_n$ | Number-average molecular weight of a given polymer |
| $M_w$ | Weight-average molecular weight of a given polymer |
| $P = M_w/M_n$ | Polydispersity of a given polymer |
| Absorption coefficient | AC = A/b, where A, absorbance, = $Log_{10}(1/T)$ and b = film thickness in microns, where T = transmittance as defined below. |

Transmittance Transmittance, T, =ratio of the radiant power transmitted by a sample to the radiant power incident on the sample and is measured for a specified wavelength $\lambda$ (e.g., nm).

Example 1

Preparation of Composition IV-A 13 g (0.1 mol) of a mixture endo- and exo-5-chloronorbornene-2 with an endo/exo ratio of 73/27 was combined at ambient temperature with 35 g (0.11 mol) of ICH$_2$C(CF$_3$)$_2$OH to which combination was added 1.5 g of 2,2'-azobis(2-methyl)propionitrile (AIBN, supplied by Aldrich, 98%) initiator. The reaction mixture was agitated at 70–80° C. under nitrogen atmosphere for 3 hours.

The reaction mixture was cooled to ambient temperature and an additional 1.5 g of AIBN was added. Heating was continued for another 3 hours and the reaction mixture was agitated for 10 hours at ambient temperature. The reaction mixture was washed with 200 mL of water, dried over MgSO$_4$ and distilled under vacuum to give 9 g (yield 21%) of product IV-A (mixture of isomers), b.p. 90–96/0.11 mm and 25 g of higher boiling point residue.

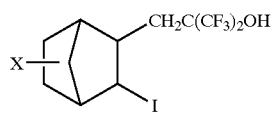

IV-A

Wherein X is chlorine.

Example 2

Reduction of Composition IV-A

Example 2a

Reduction of Composition IV-A Using Zinc 58 g of the composition (IV-A) so prepared but not distilled, was dissolved in 150 mL of ethanol (96%); the solution was added to a 3-neck flask containing 26 g of Zn dust (supplied by Acros, 97%) and equipped with water condenser, thermometer and addition funnel. The mixture was preheated to 40° C. under agitation. Hydroiodic acid (50 mL, 47 wt. %) was added slowly from an addition funnel over a period of ca. 1 hour. During addition the temperature quickly rose to 60° C. The rate of the acid addition was adjusted to maintain internal temperature of the reaction mixture at 60–70° C.

The reaction mixture was maintained at 60° C. for an additional hour.

The liquid part of the reaction mixture was decanted and the solid residue was washed with two 50 mL aliquots of ethanol. The combined ethanolic wash solutions were diluted with 1 L of water; 100 mL of CH$_2$Cl$_2$ was added; the organic layer formed thereby was separated, water was extracted with two 50 mL aliquots of CH$_2$Cl$_2$ The combined CH$_2$Cl$_2$ wash solutions were dried over MgSO$_4$, filtered, the solvent was removed under vacuum and the residue distilled under vacuum to give 18 g (45%) of the mixture of isomers represented by structure VII, b.p. 58–64/0.1 mm. The product was a liquid.

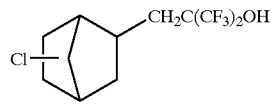

VII

Example 2b

Reduction of Composition IV-A Using Hydrogen 40 g of the purified compound represented by structure (IV-A) prepared in Example 1 was combined with 150 mL of ethanol, 20 g of K$_2$CO$_3$, and 1 g of palladium on carbon (5%, supplied by Aldrich). The mixture so prepared was agitated at 50° C. under constant 400 psi pressure of hydrogen for 12 hours. The reaction mixture was filtered through Celite® 545 (supplied by Spectrum Chem. Corp.), diluted with 500 mL of 10% hydrochloric acid, and water was extracted with three 70 mL aliquots of CH$_2$Cl$_2$. The three aliquots were combined, the solution was dried to extract any remaining water. Solvent was removed under vacuum to leave 20 g (yield 69%) of material represented by the structure (VIII)(96% purity, contained 4% of CH$_2$Cl$_2$; NMR).

Example 3

Preparation of Compound VIII

A 250-ml glass flask was charged with 32 g (0.28 mol) of potassium t-butoxide inside of a dry box with a nitrogen atmosphere. 150 mL of dry diglyme was added and mixture was agitated until all solids dissolved A solution of 18 g (0.058 mol) compound VII in 50 mL of dry diglyme was added slowly to the solution of potassium t-butoxide to maintain internal temperature of the reaction mixture <40° C. The reaction mixture was heated to 100° C. and held at that temperature for 9 hours under agitation. The reaction mixture was brought to ambient temperature, diluted with 1 L of 10% hydrochloric acid, and extracted with three 100 mL aliquots of CH$_2$Cl$_2$. The product was poorly soluble in water. The precipitated organic layer was dissolved in the first aliquot of solvent; residual product was extracted from water by the additional amounts of solvent. The aliquots following extraction were combined, was dried over MgSO$_4$, and solvent was removed under vacuum. The liquid residue was distilled using a spinning band column to give 18.5 g of a fraction with a boiling point in the range of 60–62° C./at 0.6 mm, containing about 40% diglyme. This fraction was redistilled using spinning band column to give 6 g (yield 40%) of the compound represented by the structure (VII), indicating the exo isomer at 98% purity; the remainder was diglyme. The endo isomer of VII was not detected in the distilled product using either $^{19}$F or $^1$H NMR spectroscopy.

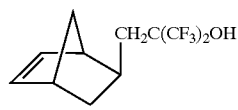

VIII

Example 4

Preparation of Composition IX

To a mixture of 17.15 g of exo-5-chloronorbornene-2 (75% purity, the rest was nortricyclyl chloride, 0.1 mol of exo-5-chloronorbornene-2) and 61.6 g (0.2 mol) of ICH$_2$C(CF$_3$)$_2$OH was added 1.64 g of AIBN initiator and the reaction mixture was heated to 70–80° C. for 9.5 hours under agitation. The combined crude reaction mixture from two separate runs was distilled under vacuum to give 181 g (yield 69% based on 0.6 mol reaction scale) of IX b.p. 87–102/0.3 mm.

IX

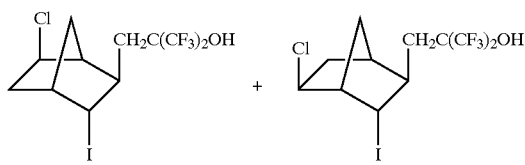

Reduction of IX.

Example 5a

Reduction Using Zinc

According to the procedure given in Example 2a, 68 g of IX was combined in 200 mL of ethanol (96%) with 31 g of Zn dust and 70 mL of hydroiodic acid. of the product represented by the structures (X) was isolated after distillation (15.5 g yield 32%; b.p. 52–60 at 0.1 mm).

X

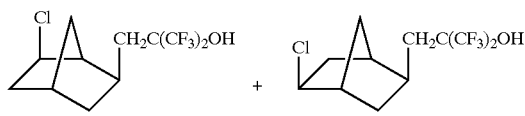

Example 5b

Reduction of IX Using Hydrogen

The purified iodide, IX, (82 g) prepared in Example 4 was dissolved in 200 mL of ethanol, and the resulting solution added to a 400 mL shaker tube. To the tube was added 50 g of solid $NaHCO_3$ and 1 g of palladium on carbon (5%, supplied by Aldrich). The reactor was cooled to −40° C., evacuated and charged with 400 psi of hydrogen and kept at 80° C. for 2 hours, then further pressurized to 900 psi of hydrogen and kept at 80° C. for 10 hours. The reaction mixture was filtered through approximately 5 cm layer of Celite[R] 545, diluted with 700 mL of water, and extracted with three 100 mL aliquots of $CH_2Cl_2$. The three 100 mL aliquots were then combined in a separate vessel and washed with two 300 mL aliquots of 0.1 molar solution of sodium thiosulfate and dried over $MgSO_4$. The solvent was removed under vacuum and the liquid residue (58 g) was distilled at 0.4 mm Hg to give 42 g (72%) of the product, X. b.p. 60–68° C. at 0.4 mm. Found: C, 42.40, H, 4.21, F, 36.82. $^1$H NMR (mixture isomers, $CDCl_3$): 1.1–2.1 (11H, m), 2.2–2.5 (2H), 2.7–2.8(1H), 3.9 (1H, m). $^{19}$F (mixture isomers, $CDCl_3$): −76.9 to −77.4 (3F, m), −77.5 to −77.9 (3F, m).

Example 6

Dehydrochlorination of X

A 1 L round bottom flask was charged with 96 g (0.86 mol) of $KOC(CH_3)_3$ inside of a nitrogen filled glove box. The flask was fitted with a thermocouple, a reflux water condenser and an addition funnel. Dry THF (250 mL) was added to the flask and the mixture so formed was agitated for 5 min to dissolve most of the solids. A solution of 44 g of the product X in 50 ml of dry THF was added dropwise over a period of 5 min. During the addition, the internal temperature rose to 45° C. The addition funnel was replaced with a glass stopper and the reaction mixture was refluxed at 69–70° C. for 15 h. Gas chromatography indicated that the conversion of X after 15 hours was >98%.

The solvent was removed under vacuum of approximately 100 to 1 mm, and the solid residue was dissolved in 700 mL of water and about 70 ml of concentrated hydrochloric acid was slowly added to the solution at 10–20° C. to achieve a pH ≈1). The reaction mixture was extracted with two 100 mL aliquots of $CH_2Cl_2$. The organic layers from the two aliquots were combined, washed with two 300 mL aliquots of 10% HCl, and dried over $MgSO_4$. The solvent was removed under vacuum to give 54 g of crude product. Combined crude product, total weight of 116 g, from two consecutive runs (scale 0.14 mol and 0.18 mol respectively) was distilled under vacuum using a spinning band column to give 80 g (91%) of (VIII), b.p. 84–84.7° C./17 mm, containing <3% of endo isomer (NMR; GC). Found: C, 47.52, H, 4.40, F, 41.59.

$^1$H NMR ($CDCl_3$): 1.4(4H, m), 1.7 (1H, s), 2.1(2H, m), 2.6(1 H, s), 2.7(1H, s), 2.8(1H, s), 6.14 (2H, m). $^{19}$F NMR ($CDCl_3$): −77.4 (6F, m) $^{13}$C NMR {H}(neat): 32.2(s); 34.5 (s), 36.7(s), 42.2 (s), 35.0 (s), 48.4 (s), 76.9 (hept, 28 Hz), 123.3 (q, 287 Hz), 136.4 (s), 136.8 (s).

Examples 7–9 and Comparative Example A

The following glossary of terms pertains to the following examples.

| | |
|---|---|
| HAdA | Hydroxyadamantyl acrylate OHKA America, Milpitas, CA |
| HFPO-dp | $[CF_3CF_2CF_2OCF(CF_3)CO_2]_2$. Prepared as described by Chengxue et. al., Journal of Organic Chemistry, vol 47, pages 2009–2013 (1982) |
| Exo-NB-$CH_2$—F—OH | 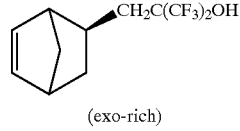<br>(exo-rich) |
| Endo/Exo-NB-$CH_2$—F—OH | 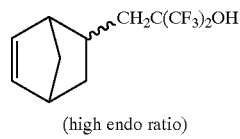<br>(high endo ratio) |
| Perkadox ® 16 N | Di-(4-tert-butylcyclohexyl) peroxydicarbonate Noury Chemical Corp., Burt, NY |
| PinAc | 2-Propenoic acid, 2-hydroxy-1,1,2-trimethylpropyl ester [CAS Reg number 97325-36-5] |
| Solkane 365 mfc | 1,1,1,3,3-Pentafluorobutane Solvay Fluor, Hannover, Germany |
| t-BuAc | tert-Butyl acrylate Aldrich Chemical Company, Milwaukee, WI |
| TFE | Tetrafluoroethylene E. I. du Pont de Nemours and Company, Wilmington, DE |
| THF | Tetrahydrofuran Aldrich Chemical Co., Milwaukee, WI |

Example 7

Synthesis of a TFE, exo-NB—$CH_2$—F—OH, t-BuAc terpolymer

A metal pressure vessel of approximate 270 mL capacity was charged with 67.12 g exo-NB—$CH_2$—F—OH prepared as described in Example 6, 0.64 g tert-butyl acrylate and 25 mL Solkane 365 mfc. The vessel was closed, cooled to about −15° C., and pressurized to 400 psi with nitrogen and vented several times. The reactor contents at about atmospheric pressure were heated to 50° C. TFE was added to a total pressure of 340 psi and a pressure regulator was set to maintain the pressure at 340 psi throughout the polymerization by adding TFE as required. A monomer feed solution (100 mL) was prepared by combining 78.01 g of the exo-NB—CH$_2$—F—OH and 8.00 g of tert-butyl acrylate in Solkane 365 mfc. The solution so prepared was pumped into the reactor at a rate of 0.10 mL/minute for 12 hours. Simultaneously, a solution of 7.3 g Perkadox®16N and 60 mL methyl acetate diluted to 100 mL with Solkane 365 mfc was pumped into the reactor at a rate of 2.0 mL/minute for 6 minutes, and then at a rate of 0.1 mL/minute for 8 hours. After 16 hours of reaction, the vessel was cooled to room temperature and vented to 1 atmosphere. The recovered polymer solution was added slowly while stirring to an excess of hexane to precipitate the polymer. Hexane is a non-solvent for the polymer. The precipitate formed thereby was filtered, washed with hexane and air dried. The resulting solid was dissolved in a mixture of THF and Solkane 365 mfc and added slowly to excess hexane. The precipitate so formed was filtered, washed with hexane and dried in a vacuum oven overnight to give 19.7 g of white polymer. From its $^{13}$C NMR spectrum, the polymer composition was found to be 36% TFE, 50% exo-NB—CH$_2$—F—OH and 14% t-BuAc. DSC: Tg=154° C. GPC: Mn=5800; Mw=7500; Mw/Mn=1.29. Anal. Found: C, 46.11; H, 4.08; F, 41.75.

Comparative Example A

Synthesis of a TFE, endo/exo NB—CH$_2$—F—OH, t-BuAc terpolymer

The procedure in Example 7 was followed except that an endo/exo-NB—CH$_2$—F—OH mixture, prepared as described by Ito et al, US 2002/0102490 was used in place of the exo-NB—CH$_2$—F—OH of Example 6. Isolated was 8.5 g of white polymer. From its $^{13}$C NMR spectrum, the polymer composition was found to be 24% TFE, 47% endo/exo-NB—CH$_2$—F—OH and 29% t-BuAc. DSC: Tg=166° C. GPC: Mn=5800; Mw=7000; Mw/Mn=1.20. Anal. Found: C, 49.03; H, 4.87; F, 36.90.

Example 8

Synthesis of a TFE, exo-NB—CH$_2$—F—OH, t-butyl acrylate terpolymer

A metal pressure vessel of approximate 270 mL capacity was charged with 67.12 g exo-NB—CH$_2$—F—OH, 0.64 g tert-butyl acrylate and 25 mL Solkane 365. The vessel was closed, cooled to about −15 ° C. and pressured to 400 psi with nitrogen and vented several times. The reactor contents were heated to 40° C. TFE was added to a pressure of 340 psi and a pressure regulator was set to maintain the pressure at 340 psi throughout the polymerization by adding TFE as required. A solution of 78.01 g of exo-NB—CH$_2$—F—OH and 8.00 g of tert-butyl acrylate diluted to 100 mL with Solkane 365 mfc was pumped into the reactor at a rate of 0.10 mL/minute for 12 hours. Simultaneously with the monomer feed solution, a 0.28 molar solution of HFPO-dp in Solkane 365 mfc was pumped into the reactor at a rate of 2.0 mL/minute for 6 minutes, and then at a rate of 0.1 mL/minute for 8 hours. After a 16 hours reaction time, the vessel was cooled to room temperature and vented to 1 atmosphere. The recovered polymer solution was added slowly to an excess of hexane while stirring. The precipitate was filtered, washed with hexane and air dried. The resulting solid was dissolved in a mixture of THF and Solkane 365 mfc and added slowly to excess to hexane. The precipitate was filtered, washed with hexane and dried in a vacuum oven overnight to give 29.5 g of white polymer. From its $^{13}$C NMR spectrum, the polymer composition was found to be 41% TFE, 47% exo-NB—CH$_2$—F—OH and 11% t-BuAc. DSC: Tg=145° C. GPC: Mn=6200; Mw=8100; Mw/Mn=1.31. Anal. Found: C, 43.22; H, 3.42; F, 43.38.

Example 9

Synthesis of a TFE, exo-NB—CH$_2$—F—OH, PinAc, and HAdA tetrapolymer

A metal pressure vessel of approximate 270 mL capacity was charged with 72.34 g exo-NB—CH$_2$—F—OH, 3.72 g PinAc, 3.20 g HADA and 35 mL Solkane 365. The vessel was closed, cooled to about −15° C. and pressured to 400 psi with nitrogen and vented several times. The reactor contents were heated to 50° C. TFE was added to a pressure of 270 psi and a pressure regulator was set to maintain the pressure at 270 psi throughout the polymerization by adding TFE as required. A solution of 47.95 g of exo-NB—CH$_2$—F—OH, 25.08 g PinAc and 21.28 g HAdA diluted to 100 mL with Solkane 365 mfc was pumped into the reactor at a rate of 0.10 mL/minute for 12 hours. Simultaneously with the monomer feed solution, a solution of 7.3 g Perkadox®16N and 60 mL methyl acetate diluted to 100 mL with Solkane 365 mfc was pumped into the reactor at a rate of 2.0 mL/minute for 6 minutes, and then at a rate of 0.1 mL/minute for 8 hours. After a 16 hours reaction time, the vessel was cooled to room temperature and vented to 1 atmosphere. The recovered polymer solution was added slowly to an excess of hexane while stirring. The precipitate was filtered, washed with hexane and air dried. The resulting solid was dissolved in a mixture of THF and Solkane 365 mfc and added slowly to excess to hexane. The precipitate was filtered, washed with hexane and dried in a vacuum oven overnight to give 80.1 g of white polymer. From its $^{13}$C NMR spectrum, the polymer composition was found to be 9% TFE, 41% exo-NB—CH$_2$—F—OH, 32% PinAc and 18% HAdA. GPC: Mn=7500; Mw=14400; Mw/Mn=1.93. Anal. Found: C, 54.86; H, 6.10; F, 24.58.

Example 10

A coating solution of the following composition was prepared and magnetically stirred overnight.

| Component | Wt. (gm) |
|---|---|
| TFE/exo-NB—CH$_2$—F—OH/ PinAc/HAdA polymer in Example 9 | 1.140 |
| 2-Heptanone | 7.980 |
| 6.82% (wt) solution of triphenylsulfonium nonaflate (Midori Kagaku Co, Ltd.) dissolved in 2-heptanone which had been filtered through a 0.45μ PTFE syringe filter. | 0.880 |

A 4 inch diameter Type "P", <100> orientation, silicon wafer was prepared by applying an hexamethyldisilazane (HMDS) prime layer using a YES-3 vapor prime oven. A 100% HMDS adhesion promoter from Arch Chemical Co. was used. The oven was programmed to give a 5 minute prime at 150–300° C.

2 mL of the above prepared coating solution was filtered through a 0.45 micrometer poly-tetrafluoroethylene (PTFE) syringe filter (Whatman Filters Co.) and deposited onto the thus prepared wafer. Spin-coating was accomplished employing a Brewer Science Inc. Model-100CB combination spin coaterthotplate. The wafer was spun at 2500 rpm for 60 seconds and then baked at 120° C. for 60 seconds.

248 nm imaging was accomplished by exposing the thus prepared coated wafer to light obtained by passing broadband UV light from an ORIEL Model-82421 Solar Simulator (1000 watt) through a 248 nm interference filter which passes about 30% of the energy at 248 nm. Exposure time was 30 seconds, providing an unattenuated dose of 45 mJ/cm$^2$. By using a mask with 18 positions of varying neutral optical density, a wide variety of exposure doses were generated. After exposure the exposed wafer was baked at 120° C. for 60 seconds.

The wafer was tray-developed for 60 sec in aqueous tetramethylammonium hydroxide (TMAH) solution (Shipley LDD-026w, 2.38% TMAH solution). A positive image was obtained with a clearing dose of ≈20 mJ/cm$^2$.

Example 11

A coating solution of the following composition was prepared and magnetically stirred overnight.

| Component | Wt. (gm) |
|---|---|
| TFE/exo-NB—CH$_2$—F—OH/PinAc/HAdA polymer in Example 9 | 1.020 |
| 2-Heptanone | 7.980 |
| t-Butyl Lithocholate | 0.120 |
| 6.82% (wt) solution of triphenylsulfonium nonaflate dissolved in 2-heptanone which had been filtered through a 0.45μ PTFE syringe filter. | 0.880 |

The wafer was prepared and processed as in Example 10. A positive image was obtained with a clearing dose of ≈9.7 mJ/cm$^2$.

Example 12

A coating solution of the following composition was prepared and magnetically stirred overnight.

| Component | Wt. (gm) |
|---|---|
| TFE/exo-NB—CH$_2$—F—OH/tBA polymer in Example 8 | 0.798 |
| 2-Heptanone | 5.586 |
| 6.82% (wt) solution of triphenylsulfonium nonaflate dissolved in 2-heptanone which had been filtered through a 0.45μ PTFE syringe filter. | 0.616 |

The wafer was prepared and processed as in Example 10. A positive image was obtained with a clearing dose of ≈4.4 mJ/cm$^2$.

Example 13

A coating solution of the following composition was prepared and magnetically stirred overnight.

| Component | Wt. (gm) |
|---|---|
| TFE/exo-NB—CH$_2$—F—OH/tBA polymer in Example 8 | 0.714 |
| 2-Heptanone | 5.586 |
| t-Butyl Lithocholate | 0.084 |
| 6.82% (wt) solution of triphenylsulfonium nonaflate dissolved in 2-heptanone which had been filtered through a 0.45μ PTFE syringe filter. | 0.616 |

The wafer was prepared and processed as in Example 10. A positive image was obtained with a clearing dose of ≈9.7 mJ/cm$^2$.

The description of illustrative and preferred embodiments of the present invention is not intended to limit the scope of the invention. Various modifications, alternative constructions and equivalents may be employed without departing from the true spirit and scope of the appended claims.

What is claimed is:

1. A composition comprising endo- and exo-2-(bicyclo[2.2.1]hept-5-en-2-yl)-2,2-fluoroalkyl-ethan-2-ol whereof the endo/exo concentration ratio is no greater than 5/95, as represented by the structure (I)

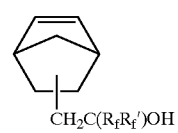

(I)

wherein the R$_f$ and R$_{f'}$ groups are the same or different fluoroalkyl groups of from 1 to about 10 carbon atoms, or taken together in cyclic form are (CF$_2$)$_n$ where n is an integer from 2 to 10.

2. The composition of claim 1 wherein the R$_f$ and R$_{f'}$ groups are perfluoromethyl.

3. A polymer made by polymerizing the composition of claim 1.

4. A copolymer made by copolymerizing the composition of claim 1 and an olefinic comonomer.

5. The copolymer of claim 4 in which the olefinic comonomer is a fluorolefin.

6. A polymer comprising about 10 mol % to about 60 mole % of a repeat unit derived from a composition comprising endo and exo monomer units represented by structure (II)

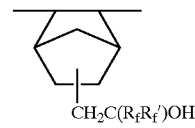

(II)

wherein the R$_f$ and R$_{f'}$ groups are the same or different fluoroalkyl groups of from 1 to 10 carbon atoms, or taken together in cyclic form are (CF$_2$)$_n$; n is an integer from 2 to 10; the monomer units of the composition having an endo/exo ratio no greater than 5/95.

7. The polymer of claim 6 further comprising a unit derived from an olefinic monomer.

8. The polymer of claim 6 in which the olefinic monomer is a fluoroolefin.

9. The polymer of claim 6 wherein at least one of R$_f$ and R$_{f'}$ is perfluoromethyl.

10. The polymer of claim 8 wherein said fluoroolefin is selected from the group consisting of tetrafluoroethylene, hexafluoropropylene, chlorotrifluoroethylene, vinylidene fluoride, vinyl fluoride, perfluoro-(2,2-dimethyl-1,3-dioxole), perfluoro-(2-methylene4-methyl-1,3-dioxolane), $CF_2=CFO(CF_2)_tCF=CF_2$, where t is 1 or 2, and $R_f\cdot OCF=CF_2$ wherein $R_f''$ is a fluoroalkyl group of from 1 to 10 carbon atoms.

11. The polymer of claim 10 wherein said fluoroolefin is tetrafluoroethylene.

12. The polymer of claim 6 further comprising a unit having a protected acidic group that forms, when photolytically activated, hydrophilic acidic groups.

13. The polymer of claim 12 wherein said protected acidic group is selected from the group consisting of esters capable of forming, or rearranging to, a tertiary cation, esters of lactone, acetal esters, β-cyclic ketone esters, α-cyclic ether esters, methoxy ethoxy ethyl methacrylate, and carbonates formed from a fluorinated alcohol and a tertiary aliphatic alcohol.

14. The polymer of claim 6 further comprising a unit derived from a monomer selected from the group consisting of tert-butyl acrylate, 2-methyl-2-adamantyl acrylate, 2-tetrahydropyranyl acrylate, 2-tetrahydrofuramyl acrylate, and 2-hydroxy-1,1,2-trimethylpropyl ester.

15. The polymer of claim 14 wherein said monomer is t-butyl acrylate or 2-methyl-2-adamantyl acrylate.

16. A process for preparing a composition comprising endo- and exo-2-bicyclo[2.2.1]hept-5-en-2-yl)-2,2-fluoroalkyl-ethan-2-ol whereof the endo/exo concentration ratio is no greater than about 5/95, the process, comprising the steps of:

contacting in the presence of a source of free radicals a substituted norbornene with $ICH_2C(R_f)(R_{f'})OH$; wherein said substituted norbornene is represented by the structure (III)

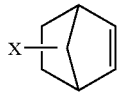
(III)

to form an iodine-containing substituted norbornane compound represented by structure (IV);

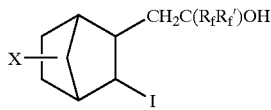
(IV)

contacting said iodine-containing compound with a reducing agent to form a substituted norbornane represented by structure (V);

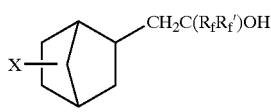
V forming an olefin from the substituted norbornane (V) to form a composition comprising endo and exo 2-(bicyclo [2.2.1]hept-5-en-2-yl)-2,2-perfluoroalkyl-ethan-2-ol, whereof the endo/exo concentration ratio is no greater than 5/95 as represented by the structure (I);

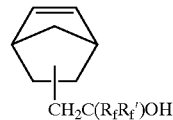
(I)

wherein in the foregoing structures the $R_f$ and $R_{f'}$ groups are the same or different fluoroalkyl groups of from 1 to 10 carbon atoms, or taken together in cyclic form are $(CF_2)_n$, n is an integer from 2 to 10, and wherein X is selected from the group consisting of Cl, Br, and $R_8SO_2$—O—, where $R_8$ is an alkyl-, fluoroalkyl, aryl or fluoroaryl radical.

17. The process of claim 16 wherein at least one of $R_f$ and $R_{f'}$ is perfluoromethyl.

18. The process of claim 16 wherein X is Cl.

19. The process of claim 16 wherein the Cl is predominantly in the exo position.

20. The process of claim 16 wherein said iodine-containing compound is contacted with a reducing agent.

21. The process of claim 16 wherein said solvent is selected from the group consisting of water, alcohol, tetrahydrofuran and a glyme; said hydrogenation catalyst is Pd or Pt, and the base is selected from the group consisting of sodium and potassium bicarbonate, sodium and potassium carbonate, and an amine.

22. A photoresist suitable for use in the preparation of electronic circuits said photoresist comprising a photoactive agent and a polymer compromising 10 mol-% to 60 mol-% of a repeat unit represented by the structure (II)

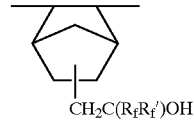
(II)

and whereof said repeat unit is derived from a composition comprising endo- and exo-2-(bicyclo[2.2.1]hept-5-en-2-yl)-2,2-fluoroalkyl-ethan-2-ol, as represented by the structure (I)

(I)

wherein the $R_f$ and $R_{f'}$ groups are the same or different fluoroalkyl groups of from 1 to about 10 carbon atoms, or taken together in cyclic form are $(CF_2)_n$ where n is an integer from 2 to 10, whereof the endo/exo ratio is no greater than 5/95.

23. The photoresist of claim 22 wherein at least one of $R_f$ and $R_{f'}$ is perfluoromethyl.

24. The photoresist of claim 22 wherein said polymer further comprises a unit derived from a fluoroolefin selected from the group consisting of tetrafluoroethylene, hexafluoropropylene, chlorotrifluoroethylene, vinylidene fluoride, vinyl fluoride, perfluoro-(2,2-dimethyl-1,3-dioxole), perfluoro-(2-methylene4-methyl-1,3-dioxolane), $CF_2=CFO(CF_2)_tCF=CF_2$, where t is 1 or 2, and $R_f\cdot OCF=CF_2$ wherein $R_f''$ is a fluoroalkyl group of from 1 to 10 carbon atoms.

25. The photoresist of claim 24 wherein said fluoroolefin is tetrafluoroethylene.

26. The photoresist of claim 22 wherein said polymer further comprises a unit having a protected acidic group.

27. The photoresist of claim 26 wherein said acidic group is a fluorinated alcohol group.

28. The photoresist of claim 26 wherein said protected acidic group is selected from the group consisting of esters capable of forming, or rearranging to, a tertiary cation, esters of lactone, acetal esters, β-cyclic ketone esters, α-cyclic ether esters, methoxy ethoxy ethyl methacrylate, and carbonates formed from a fluorinated alcohol and a tertiary aliphatic alcohol.

29. The photoresist of claim 22 wherein said polymer further comprises a unit derived from one or more of tert-butyl acrylate, 2-methyl-2-adamantyl acrylate, 2-tetrahydropyranyl acrylate, 2-tetrahydrofuramyl acrylate, and 2-hydroxy-1,1,2-trimethylpropyl ester.

30. The photoresist of claim 22 wherein said unit is derived from t-butyl acrylate or 2-methyl-2-adamantyl acrylate.

31. An article comprising a semiconducting substrate having a surface, and a photoresist film disposed upon at least a portion of said surface, said photoresist film comprising a photoactive agent and a polymer comprising about 10 mol-% to 60 mol-% of a repeat unit represented by the structure (II)

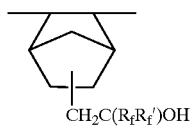

and whereof said repeat unit is derived from a composition comprising endo- and exo-2-(bicyclo[2.2.1]hept-5-en-2-yl)-2,2-fluoroalkyl-ethan-2-ol, as represented by the structure (I)

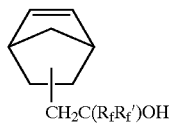

wherein the $R_f$ and $R_{f'}$ groups are the same or different fluoroalkyl groups of from 1 to about 10 carbon atoms, or taken together in cyclic form are $(CF_2)_n$ where n is an integer from 2 to 10, whereof the endo/exo ratio is no greater than 5/95.

32. The article of claim 31 wherein at least one of $R_f$ and $R_{f'}$ is perfluoromethyl.

33. The article of claim 31 wherein said polymer further comprises repeat units derived from a fluoroolefin selected from the group consisting of tetrafluoroethylene, hexafluoropropylene, chlorotrifluoroethylene, vinylidene fluoride, vinyl fluoride, perfluoro-(2,2-dimethyl-1,3-dioxole), perfluoro-(2-methylene-4-methyl-1,3-dioxolane), $CF_2=CFO(CF_2)_tCF=CF_2$, where t is 1 or 2, and $R_f''OCF=CF_2$ wherein $R_f''$ is a fluoroalkyl group of from 1 to 10 carbon atoms.

34. The article of claim 33 wherein said fluoroolefin is tetrafluoroethylene.

35. The article of claim 31 wherein said polymer further comprises a repeat unit derived from a monomer having a protected acidic group.

36. The article of claim 35 wherein said acidic group is a fluorinated alcohol group.

37. The article of claim 35 wherein said protected acidic group is selected from the group consisting of esters capable of forming, or rearranging to, a tertiary cation, esters of lactone, acetal esters, β-cyclic ketone esters, α-cyclic ether esters, methoxy ethoxy ethyl methacrylate, and carbonates formed from a fluorinated alcohol and a tertiary aliphatic alcohol.

38. The article of claim 31 further comprising a unit derived from a monomer selected from the group consisting of tert-butyl acrylate, 2-methyl-2-adamantyl acrylate, 2-tetrahydropyranyl acrylate, 2-tetrahydrofuramyl acrylate, and 2-hydroxy-1,1,2-trimethylpropyl ester.

39. The article of claim 38 wherein said monomer is t-butyl acrylate or 2-methyl-2-adamantyl acrylate.

40. The article of claim 31 wherein said substrate comprises silicon.

41. A process for preparing a patterned article the process comprising:

forming a target surface by disposing upon a semiconducting substrate a photoresist film comprising a photoactive agent and a polymer comprising about 10 mol-% to 60 mol-% of a repeat unit represented by the structure (II)

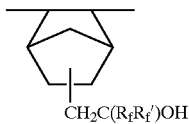

whereof said repeat unit is derived from a composition comprising endo- and exo-2-(bicyclo[2.2.1]hept-5-en-2-yl)-2,2-fluoroalkyl-ethan-2-ol, as represented by the structure (I)

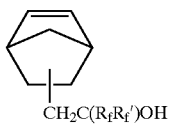

wherein the $R_f$ and $R_{f'}$ groups are the same or different fluoroalkyl groups of from 1 to about 10 carbon atoms, or taken together in cyclic form are $(CF_2)_n$ where n is an integer from 2 to 10, whereof the endo/exo ratio is no greater than 5/95;

illuminating said target surface in such a manner as to form a pattern of shadowed and illuminated areas, the illuminating step causing a change in solubility of said polymer;

removing the soluble portions of said polymer, thereby producing a patterned article.

42. The process of claim 41 in which the process further comprises after the illuminating step a step of heating the target surface.

43. The process of claim 41 wherein at least one of $R_f$ and $R_{f'}$ is perfluoromethyl.

44. The process of claim 41 wherein said polymer further comprises a unit derived from a fluoroolefin selected from the group consisting of tetrafluoroethylene, hexafluoropropylene, chlorotrifluoroethylene, vinylidene fluoride, vinyl fluoride, perfluoro-(2,2-dimethyl-1,3-dioxole), perfluoro-(2-methylene4-methyl-1,3-dioxolane), $CF_2=CFO(CF_2)_tCF=CF_2$, where t is 1 or 2, and $R_f''OCF=CF_2$ wherein $R_f''$ is a fluoroalkyl group of from 1 to 10 carbon atoms.

45. The process of claim 44 wherein said fluoroolefin is tetrafluoroethylene.

46. The process of claim 41 wherein said polymer further comprises a unit having a protected acidic group that forms, when photolytically activated, hydrophilic acidic groups which enable development of resist coatings.

47. The process of claim 46 wherein said acidic group is a fluorinated alcohol group.

48. The process of claim 46 wherein said protected acidic group is selected from the group consisting of an ester capable of forming, or rearranging to, a tertiary cation, an ester of lactone, an acetal ester, a β-cyclic ketone ester, an α-cyclic ether ester, a methoxy ethoxy ethyl methacrylate, and a carbonate formed from a fluorinated alcohol and a tertiary aliphatic alcohol.

49. The process of claim 41 wherein said polymer further comprises a unit derived from a monomer selected from the group consisting of tert-butyl acrylate, 2-methyl-2-adamantyl acrylate, 2-tetrahydropyranyl acrylate, 2-tetrahydrofuramyl acrylate, and 2-hydroxy-1,1,2-trimethylpropyl ester.

50. The process of claim 49 wherein said monomer is t-butyl acrylate or 2-methyl-2-adamantyl acrylate.

51. The process of claim 41 wherein said substrate comprises silicon.

* * * * *

UNITED STATES PATENT AND TRADEMARK OFFICE
CERTIFICATE OF CORRECTION

PATENT NO. : 6,875,555 B1
APPLICATION NO. : 10/664303
DATED : April 5, 2005
INVENTOR(S) : Andrew Edward Feiring, Viacheslav A. Petrov and Frank Leonard Schadt, III It is certified that error appears in the above-identified patent and that said Letters Patent is hereby corrected as shown below:

Column 24, line 34, 38: " $R_f$ and $R_f$ " should read -- $R_f$ and $R_f'$ --

Column 24, line 45: "comonomer is a fluorolefin" should read --comonomer is a fluoroolefin--

Column 24, Structure I and Structure II: that portion of the formula reading "$CH_2C(R_fR_f')OH$" should read --$CH_2C(R_f)(R_f')OH$--

Column 24, line 67: " $R_f$ is perfluoromethyl." should read --$R_f'$ is perfluoromethyl--

Column 25, line 5: "dioxole), perfluoro-(2-methylene4-methyl-1,3-dioxolane)," should read --dioxole), perfluoro-(2-methylene-4-methyl-1,3-dioxolane),--

Column 25, line 7: "$R_f$-OCF=CF$_2$ wherein $R_f$ is a fluoroalkyl" should read --$R_f''$OCF=CF$_2$ wherein $R_f''$--

Column 25, line 24: "2-tetrahydropyranyl acrylate, 2-tetrahydrofuramyl acrylate" should read --2-tetrahydropyranyl acrylate, 2-tetrahydrofuranyl acrylate--

Column 25, line 29: "endo- and exo-2-bicyclo[2.2.1]hept-5-en-2-yl)-2,2-" should read --endo- and exo-2-(bicyclo[2.2.1]hept-5-en-2-yl)-2,2--

Column 25, line 34: "substituted norbornene with $ICH_2C(R_f)(R_f)OH$; :" should read --substituted norbornene with $ICH_2C(R_f)(R_f')OH$;--

Column 25, line 48, 58: that portion of the structure reading "$CH_2C(R_fR_f')OH$" should read --$CH_2C(R_f)(R_f')OH$--

Column 26, line 6: that portion of the structure reading "$CH_2C(R_fR_f')OH$" should read --$CH_2C(R_f)(R_f')OH$--

Column 26, line 16, 56: "$R_f$ is perfluoromethyl." should read -- $R_f'$ is perfluoromethyl--

Column 26, line 62: "dioxole), perfluoro-(2-methylene4-methyl-1,3-dioxolane)," should read --dioxole), perfluoro-(2-methylene-4-methyl-1,3-dioxolane),--

Column 26, line 63: "$R_f$-OCF=CF$_2$ wherein $R_f''$ is a fluoroalkyl group of from 1" should read --$R_f''$OCF=CF$_2$ wherein $R_f''$ is a fluoroalkyl group of from 1--

UNITED STATES PATENT AND TRADEMARK OFFICE
CERTIFICATE OF CORRECTION

PATENT NO. : 6,875,555 B1
APPLICATION NO. : 10/664303
DATED : April 5, 2005
INVENTOR(S) : Andrew Edward Feiring, Viacheslav A. Petrov and Frank Leonard Schadt, III It is certified that error appears in the above-identified patent and that said Letters Patent is hereby corrected as shown below:

Column 27, line 15: "2-tetrahydropyranyl acrylate, 2-tetrahydrofuramyl acrylate" should read --2-tetrahydropyranyl acrylate, 2-tetrahydrofuranyl acrylate--

Column 27, line 30, 43: that portion of the structure reading "$CH_2C(R_fR_f')OH$" should read --$CH_2C(R_f)(R_f')OH$--

Column 27, line 45: "wherein the $R_f$ and $R_f$ groups" should read --wherein the $R_f$ and $R_f'$ groups--

Column 27, line 51: " $R_{f'}$ is perfluoromethyl." should read --$R_f'$ is perfluoromethyl--

Column 28, line 11: "2-tetrahydropyranyl acrylate, 2-tetrahydrofuramyl acrylate" should read --2-tetrahydropyranyl acrylate, 2-tetrahydrofuranyl acrylate--

Column 28, line 29, 40: that portion of the structure reading "$CH_2C(R_fR_f')OH$" should read --$CH_2C(R_f)(R_f')OH$--

Column 28, line 43: "wherein the $R_f$ and $R_f$ groups" should read --wherein the $R_f$ and $R_f'$ groups--

Column 28, line 58: "$R_{f'}$ is perfluoromethyl." should read --$R_f'$ is perfluoromethyl--

Column 28, line 64: "dioxole), perfluoro-(2-methylene4-methyl-1,3-dioxolane)," should read --dioxole), perfluoro-(2-methylene-4-methyl-1,3-dioxolane),--

Column 30, line 7: "2 tetrahydrofuramyl acrylate, and 2-hydroxy-1,1,2-" should read --2-tetrahydrofuranyl acrylate, and 2-hydroxy-1,1,2- --

Column 2, lines 7, 22, 48, 58: that portion of the structure reading "$CH_2C(R_fR_f')OH$" should read --$CH_2C(R_f)(R_f')OH$--

Column 3, lines 6, 26, 39, 60: that portion of the structure reading "$CH_2C(R_fR_f')OH$" should read --$CH_2C(R_f)(R_f')OH$--

Column 4, line 7, 24, 36: that portion of the structure reading "$CH_2C(R_fR_f')OH$" should read --$CH_2C(R_f)(R_f')OH$--

UNITED STATES PATENT AND TRADEMARK OFFICE
CERTIFICATE OF CORRECTION

PATENT NO.        : 6,875,555 B1
APPLICATION NO. : 10/664303
DATED             : April 5, 2005
INVENTOR(S)       : Andrew Edward Feiring, Viacheslav A. Petrov and Frank Leonard Schadt, III It is certified that error appears in the above-identified patent and that said Letters Patent is hereby corrected as shown below:

Column 5, line 41: that portion of the structure reading "$CH_2C(R_fR_f')OH$" should read --$CH_2C(R_f)(R_f')OH$--

Column 6, line 18: that portion of the structure reading "$CH_2C(R_fR_f')OH$" should read --$CH_2C(R_f)(R_f')OH$--

Column 10, line 13, 60: that portion of the structure reading "$CH_2C(R_fR_f')OH$" should read --$CH_2C(R_f)(R_f')OH$--

Claim 1: that portion of the structure reading "$CH_2C(R_fR_f')OH$" should read --$CH_2C(R_f)(R_f')OH$--.

Claim 1: "wherein the $R_f$ and $R_f$ groups" should read --wherein the $R_f$ and $R_f'$ groups--.

Claim 2: "wherein the $R_f$ and $R_f$ groups" should read --wherein the $R_f$ and $R_f'$ groups--.

Claim 5: "comonomer is a fluorolefin" should read --comonomer is a fluoroolefin--.

Claim 6: that portion of the structure reading "$CH_2C(R_fR_f')OH$" should read --$CH_2C(R_f)(R_f')OH$--.

Claim 6: "wherein the $R_f$ and $R_f$ groups" should read --wherein the $R_f$ and $R_f'$ groups--.

Claim 9: "wherein at least one of $R_f$ and $R_f$ is perfluoromethyl" should read --wherein at least one of $R_f$ and $R_f'$ is perfluoromethyl--.

Claim 10: "perfluoro- (2-methylene4-methyl-l,3-dioxolane)," should read --perfluoro- (2-methylene-4-methyl-1,3-dioxolane) , --.

Claim 10: "and $R_{f''}OCF==CF_2$ wherein $R^{f''}$ is" should read --and $R_{f''}OCF==CF_2$ wherein $R^{f''}$ is--.

Claim 14: "2-tetrahydrofuramyl acrylate" should read -- 2-tetrahydrofuranyl acrylate--.

Claim 16: that portion of the structure reading "$CH_2C(R_fR_f')OH$" should read --$CH_2C(R_f)(R_f')OH$--.

UNITED STATES PATENT AND TRADEMARK OFFICE
CERTIFICATE OF CORRECTION

PATENT NO. : 6,875,555 B1
APPLICATION NO. : 10/664303
DATED : April 5, 2005
INVENTOR(S) : Andrew Edward Feiring, Viacheslav A. Petrov and Frank Leonard Schadt, III It is certified that error appears in the above-identified patent and that said Letters Patent is hereby corrected as shown below:

| | |
|---|---|
| Claim 16: | "and exo-2-bicyclo[2.2.1]hept-5-en-2-yl) -2,2-fluoroalkyl-ethan-2-ol whereof" should read --and exo-2- (bicyclo[2.2.1]hept-5-en-2-yl) -2,2-fluoroalkyl-ethan-2-ol whereof--. |
| Claim 16: | "wherein in the foregoing structures the $R_f$ and $R_{f'}$ groups" should read --wherein in the foregoing structures the $R_f$ and $R_f{'}$ groups--. |
| Claim 17: | "wherein at least one of $R_f$ and $R_{f'}$ is perfluoromethyl" should read --wherein at least one of $R_f$ and $R_f{'}$ is perfluoromethyl--. |
| Claim 22: | that portion of the structure reading "CH$_2$C(R$_f$R$_f{'}$)OH" should read --CH$_2$C(R$_f$)(R$_f{'}$)OH-- |
| Claim 23: | "wherein at least one of $R_f$ and $R_{f'}$ is perfluoromethyl" should read --wherein at least one of $R_f$ and $R_f{'}$ is perfluoromethyl--. |
| Claim 24: | "perfluoro-(2-methylene4-methyl-1,3-dioxolane)," should read --perfluoro-(2-methylene-4-methyl-1,3-dioxolane),--. |
| Claim 24: | "and $R_{f''}$OCF==CF$_2$ wherein $R^{f''}$ is" should read --and $R_f{''}$OCF==CF$_2$ wherein $R^{f''}$ is--. |
| Claim 29: | "2-tetrahydrofuramyl acrylate" should read -- 2-tetrahydrofuranyl acrylate--. |
| Claim 31: | that portion of the structure reading "CH$_2$C(R$_f$R$_f{'}$)OH" should read --CH$_2$C(R$_f$)(R$_f{'}$)OH-- |
| Claim 31: | "wherein the $R_f$ and $R_{f'}$ groups" should read --wherein the $R_f$ and $R_f{'}$ groups--. |
| Claim 32: | "wherein at least one of $R_f$ and $R_{f'}$ is perfluoromethyl" should read --wherein at least one of $R_f$ and $R_f{'}$ is perfluoromethyl--. |
| Claim 38: | "2-tetrahydrofuramyl acrylate" should read -- 2-tetrahydrofuranyl acrylate--. |
| Claim 41: | that portion of the structure reading "CH$_2$C(R$_f$R$_f{'}$)OH" should read --CH$_2$C(R$_f$)(R$_f{'}$)OH-- |

UNITED STATES PATENT AND TRADEMARK OFFICE
CERTIFICATE OF CORRECTION

PATENT NO. : 6,875,555 B1
APPLICATION NO. : 10/664303
DATED : April 5, 2005
INVENTOR(S) : Andrew Edward Feiring, Viacheslav A. Petrov and Frank Leonard Schadt, III It is certified that error appears in the above-identified patent and that said Letters Patent is hereby corrected as shown below:

Claim 41: "wherein the $R_f$ and $R_{f'}$ groups" should read --wherein the $R_f$ and $R_f'$ groups--.

Claim 43: "wherein at least one of $R_f$ and $R_{f'}$ is perfluoromethyl" should read --wherein at least one of $R_f$ and $R_f'$ is perfluoromethyl--.

Claim 44: "perfluoro-(2-methylene4-methyl-1,3-dioxolane)," should read --perfluoro-(2-methylene-4-methyl-1,3-dioxolane),--.

Claim 49: "2-tetrahydrofuramyl acrylate" should read -- 2-tetrahydrofuranyl acrylate--.

Signed and Sealed this

Twenty-ninth Day of May, 2007

JON W. DUDAS
*Director of the United States Patent and Trademark Office*